United States Patent
Shapira

[11] Patent Number: 5,913,859
[45] Date of Patent: Jun. 22, 1999

[54] APPARATUS FOR EXTRACTING BONE MARROW

[76] Inventor: Ira L. Shapira, 3223 Dato, Highland Park, Ill. 60035

[21] Appl. No.: 08/886,173

[22] Filed: Jul. 1, 1997

[51] Int. Cl.⁶ .................................................. A61B 17/16
[52] U.S. Cl. .............................. 606/80; 606/180; 433/82; 433/114
[58] Field of Search .................................. 600/562–568; 606/79, 80, 85, 167, 169, 170, 180; 433/82, 114

[56] References Cited

U.S. PATENT DOCUMENTS

| | | | |
|---|---|---|---|
| 2,426,535 | 8/1947 | Turkel | 600/567 |
| 2,496,111 | 1/1950 | Turkel | 600/567 |
| 3,587,560 | 6/1971 | Glassman | 600/566 |
| 3,745,655 | 7/1973 | Malmin | 433/81 |
| 3,807,048 | 4/1974 | Malmin | 433/81 |
| 3,816,921 | 6/1974 | Malmin | 433/81 |
| 3,863,635 | 2/1975 | Swatman | 604/119 |
| 3,871,099 | 3/1975 | Kahn | 433/224 |
| 3,937,222 | 2/1976 | Banko | 606/170 |
| 4,176,453 | 12/1979 | Abbott | 433/82 |
| 4,266,555 | 5/1981 | Jamshidi | 600/566 |
| 4,469,109 | 9/1984 | Mehl | 600/566 |
| 4,487,209 | 12/1984 | Mehl | 600/567 |
| 4,543,966 | 10/1985 | Islam et al. | 600/567 |
| 4,564,374 | 1/1986 | Hofmann | 95/24 |
| 4,840,184 | 6/1989 | Garg | 600/566 |
| 4,922,602 | 5/1990 | Mehl | 29/460 |
| 5,012,818 | 5/1991 | Joishy | 600/567 |
| 5,122,153 | 6/1992 | Harrel | 606/180 |
| 5,295,830 | 3/1994 | Shen et al. | 433/116 |
| 5,357,974 | 10/1994 | Baldridge | 600/567 |
| 5,403,276 | 4/1995 | Schechter et al. | 604/22 |

OTHER PUBLICATIONS

Schroeder et al., *Oral Implantology*, pp. 66–71, 118–151, 178–187, 202–217, and 228–243 (Georg Thieme Verlag, 1991).

*Primary Examiner*—Michael Buiz
*Assistant Examiner*—David O. Reip
*Attorney, Agent, or Firm*—Marshall, O'Toole, Gerstein, Murray & Borun

[57] ABSTRACT

Methods and apparatus are presented for extracting and collecting bone marrow from the jawbone of a patient before, during, or after dental procedures. The method and apparatus further provides a readily accessible, and easily harvested, source of bone marrow without the drawbacks of current extraction methods.

8 Claims, 3 Drawing Sheets

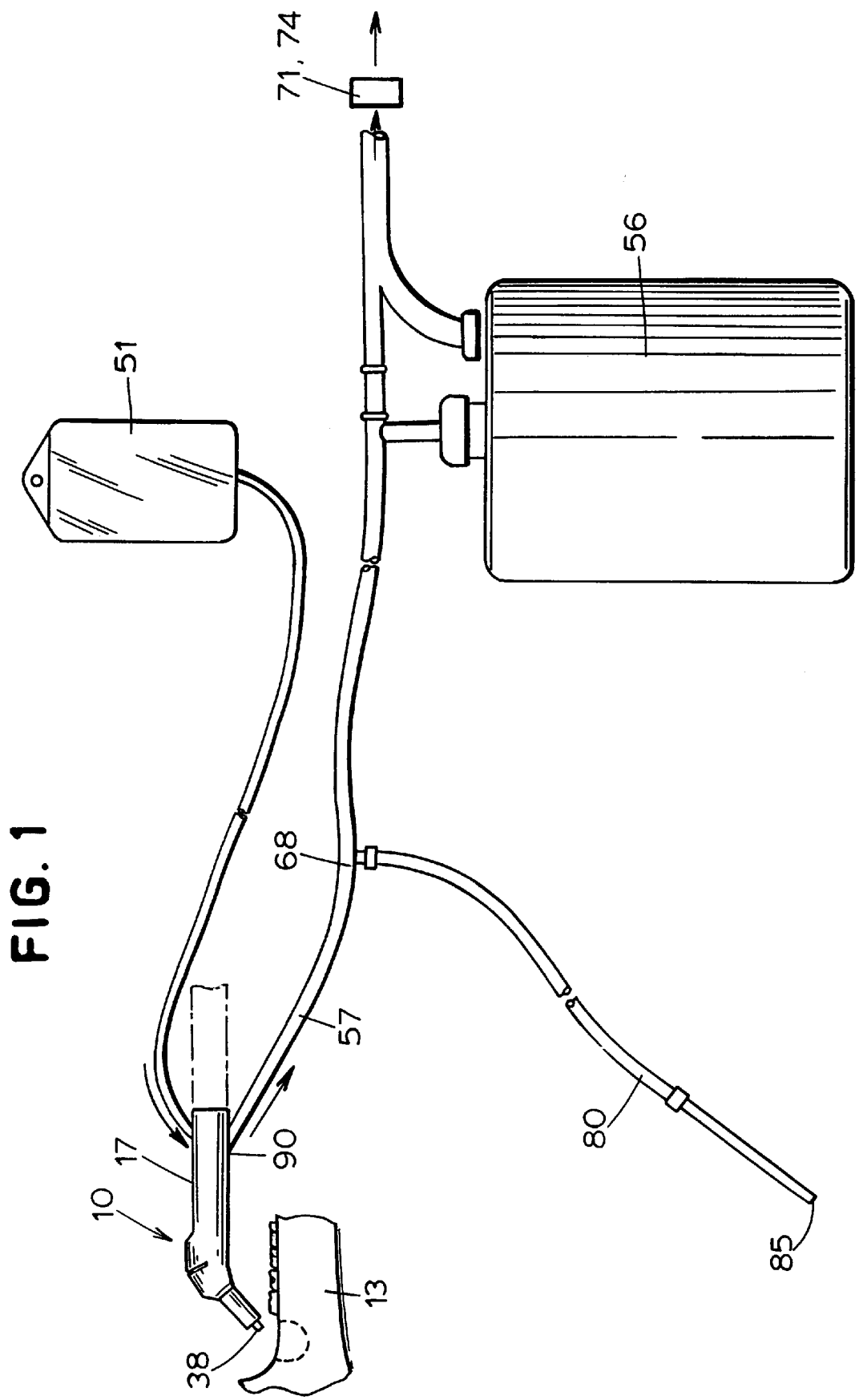

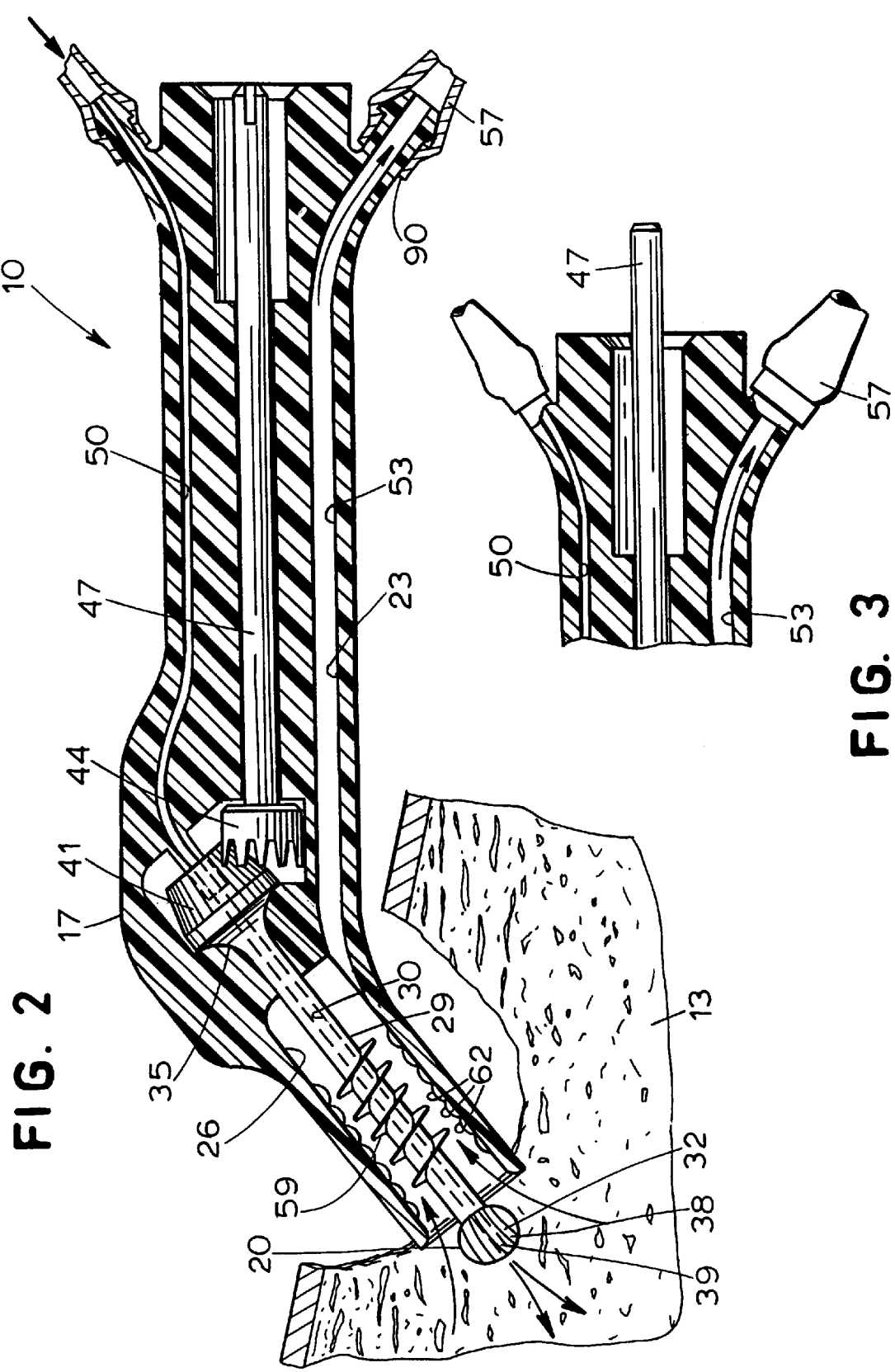

APPARATUS FOR EXTRACTING BONE MARROW

FIELD OF INVENTION

The present invention relates generally to methods and apparatus for recovering bone marrow from a patient and subsequent collection and storage. More specifically, the present invention relates to a method of obtaining bone marrow and bone marrow fluid from the jawbone of a patient with relative ease and minor discomfort before, during, or after dental procedures, such as the removal of impacted or redundant third molars or bicuspids for long term storage and/or for bone typing.

BACKGROUND OF THE INVENTION

There are a number of diseases in which the bone marrow is defective, such as aplastic anemia, some forms of leukemia, and deficiencies in the bone marrow caused by cancer treatments with drugs and irradiation. The treatment of choice for these diseases is bone marrow transplantation, provided a genetically compatible donor can be found. For instance, bone marrow transplants are significantly reducing the death toll from childhood leukemias.

Bone marrow, also called myeloid tissue, is a soft, gelatinous tissue that fills the cavity of the bones. Human bone consists of a hard outer cortex and a soft medullary cavity that contains bone marrow. Bone marrow consists of stroma, or supporting tissues which have spaces packed by blood cells. Bone marrow is either red or yellow, depending upon the preponderance of vascular (red) or fatty (yellow) tissue. In humans, the red bone marrow forms all of the blood cells with the exception of the lymphocytes, which are produced in the marrow and reach their mature form in the lymphoid organs. Yellow bone marrow serves primarily as a storehouse for fats, but may be converted to red marrow under certain conditions, such as severe blood loss or fever. At birth, and until about the age of seven, all human marrow is red, as the need for new blood formation is high. Thereafter, fat tissue gradually replaces the red marrow, which in adults is found in the vertebrae, hips, breast bone, ribs, and skull, and at the ends of the long bones of the arms and legs, other cancellous, or spongy bones, and the central cavities of the long bones. In mammals, blood formation in adults takes place predominantly in the marrow. Because the white blood cells produced in the bone marrow are involved in the body's immune defenses, marrow transplants have been used to treat certain types of immune deficiencies. The sensitivity of marrow to damage by radiation and some anticancer drugs accounts for the tendency of these treatments to impair immunity.

Bone marrow transplants can be divided into three groups according to the source of the marrow for transplantation. They are called autologous, syngeneic, or allogeneic. Autologous transplantation means that the bone marrow has been received directly from the recipient, and will be an exact genetic match. A syngeneic transplant comes from an identical twin of the recipient and will also be an exact genetic match. However, for allogeneic transplants, the bone marrow is provided by another person, and the possibility of exact genetic matching is very low.

It is reported that approximately 12,000 bone marrow transplants were performed in 1992, approximately half of which were allogeneic and half autologous. Autologous transplantation has grown significantly during the past several years as improvements in procedures are made. The number of patients receiving allogeneic transplants is also rising due in large part because donor registries have increased the number of readily available donors. Advances in bone marrow transplantation techniques will likely continue to expand the use of the bone marrow transplant procedure.

Generally, the recipient's sibling or parent will serve as the best source as the donor because of the high possibility of genetic matching. However, there are many cases where neither the parent nor the sibling will be a compatible genetic match for the recipient. There has been a recent increase in the use of bone marrow from unrelated donors which can provide genetic compatibility between the donor and recipient. This increase has been made possible through the existence of large bone marrow registries, such as the National Marrow Donor Program, and the American Bone Marrow Donor Registry. The drawback to these registries are the insufficient number of donors that genetically match closely enough with potential recipients to be of use.

The success of the bone marrow transplantation technique depends heavily on genetically cross-matching the donor marrow cells to those of the recipient to prevent rejection. There is a significant tendency for the recipient patient to reject an allografted marrow because parts of the donor marrow will attack their new host. There is an additional hazard because immune system cells in a marrow graft can react against the patient's tissues, causing serious and sometimes fatal graft versus host disease. The ability to accept a bone marrow transplant (graft) from a donor, is dependent on the recipient sharing all of the donor's histocompatibility genes. To avoid graft versus host rejection in the past, special immunosuppressive treatment has been given. The use of monoclonal antibodies to selectively remove harmful lymphocytes from the donor marrow has been successful in some cases to prevent graft versus host disease. However, the risk remains that unless the bone marrow source is from the patient himself, an identical twin, sibling, parent, or other genetically compatible donor, that the bone marrow transplantation cannot take place because it will result in graft versus host rejection, and the failure of the treatment, and possibly the death of the recipient.

Therefore, there is a significant need to collect and store genetically compatible bone marrow for use in cases where bone marrow transplantation is necessary to save the life of an individual. Because of the significant possibility that a donor cannot be found which is a close genetic match to the recipient, there is a need to collect and store an individual's own bone marrow while that individual is still healthy. If this is done, there will be a complete genetic match, and the dangers of graft versus host rejection will be eliminated which increases the success of the treatment.

The collection of bone marrow for transplantation purposes is usually accomplished by inserting a needle into a donor's hip or pelvic bone. Several small incisions are made in the pelvic area, and the needle is inserted through these incisions approximately 25 to 30 times to withdrawn the bone marrow from the bones. The extraction process typically lasts at least one hour or more, or until approximately 500 to 1000 milliliters of the donor's marrow is withdrawn.

The donor will fully recover in approximately a few weeks when all the donated marrow has been replaced within the body. However, the extraction process is painful and there is typically soreness around the incisions until healing can occur. Typically, the donors also feel fatigued for some time after the procedure. The side effects to having donated bone marrow can vary from donor to donor. Infection from the incision is always a possibility. Additionally, blood loss can also occur, and proper medical attention is required. It is recommended that donors routinely store supplies of their own blood for infusion during and after the extraction procedure in cases of emergencies.

Bone marrow can be obtained through biopsy or aspiration from the sternum or the calvarium in adults, and in long bones, such as the femur and tibia, in adolescents. Biopsy needles for extraction of solid bone marrow are known. Examples of such biopsy needles are U.S. Pat. Nos. 2,426,535; 2,496,111; 4,266,555; 4,543,966; 4,487,209; 4,840,184; and 4,922,602, which show the overall structure and orientation of the components. Needles used for aspiration of liquid bone marrow are disclosed in U.S. Pat. No. 4,469,109. Needles designed to both biopsy and aspirate bone marrow are disclosed in U.S. Pat. Nos. 2,496,111; 3,587,560; 5,012,818; and 5,357,974.

There is a need for bone marrow extraction techniques that avoid the considerable inconvenience, discomfort, and pain due to current bone marrow extraction procedures and aspiration methods. Therefore, there is also a need to provide a method and apparatus to obtain both solid and liquid bone marrow from a donor with minimal intrusion and pain. There is also a need for the bone marrow to be stored for later use and is accomplished with relative ease.

The present invention provides for a dental apparatus used for extracting the bone marrow that includes a means to bore a hole in the jawbone of a patient and to immediately collect the bone marrow in a specialized collection means all in one system. Another embodiment of the apparatus of this invention includes a bone marrow apparatus that has various sources of solution supply and collectors for the purpose of preparing the collected bone marrow for storage, preservation, and subsequent use.

The present invention provides methods and apparatus for the extraction of bone marrow from the jawbone of the donor, which will eliminate the problems often associated with obtaining bone marrow from conventional methods. It should be noted that literally millions of dental extractions of third molars and bicuspids in young, healthy adults and adolescents are performed each year. Thus, the collection, typing, and storage of bone marrow obtained during this procedure provides an immediate source of highly desirable autologous bone marrow for long-term storage. It also provides a means for obtaining allogeneic bone marrow for registry and storage in National Registries which will provide greater access for everyone to bone marrow of perfect or near-perfect genetic match to potential recipients.

The invention further provides a method for providing an easily obtainable source of bone marrow, that requires no hospitalization, minimal discomfort, and provides no scarring as is common in the conventional extraction procedures. It also provides for the ability of an individual to collect and store his own bone marrow before the onset of any disease, such as childhood leukemias, which usually occurs between the ages of 15 and 30.

SUMMARY OF THE INVENTION

The present invention provides embodiments directed to a novel and improved method and apparatus for bone marrow extraction. A method for extracting and collecting bone marrow from a jawbone of a patient comprises the steps of boring a hole in the jawbone to a depth sufficient to form a jawbone bone marrow extraction site, extracting the bone marrow from the jawbone bone marrow extraction site, and collecting and storing the bone marrow in a collection chamber.

The method may further comprise the step of infusing a solution into a void in the jawbone resulting from the bone marrow extracting step. The solution may be selected from the group consisting of anticoagulant containing saline solution and electrolyte solution.

The method may include the steps of mixing the bone marrow with a liquid to form a mixture, transferring the mixture to the collection chamber, and isolating the bone marrow from the mixture to form isolated bone marrow. The method may further comprises the steps of preserving the isolated bone marrow with a preservative to form preserved bone marrow and storing the preserved bone marrow.

Another method for extracting and collecting bone marrow from the jawbone of a patient comprises the steps of: boring a hole in the jawbone to form a jawbone bone marrow extraction site; introducing a biopsy needle into the jawbone bone marrow extraction site, wherein the biopsy needle is connected to a suction source; penetrating a medullary cavity of the jawbone bone marrow extraction site with the biopsy needle; collecting solid bone marrow through the biopsy needle; penetrating the medullary cavity with the biopsy needle; breaking marrow stroma with the biopsy needle; activating a pump to aspirate liquid bone marrow from the broken marrow stroma; and collecting the liquid bone marrow through biopsy needle.

This method may further comprise the step of selectively activating a valve to selectively generate suction in the suction tube.

Methods of the invention comprise the steps of withdrawing bone marrow from the jawbone of a patient and collecting the bone marrow in such a way as to eliminate bone marrow aspiration pain. The method also provides for the extraction and collection of the bone marrow for long-term storage and personal banking following dental extraction or surgery. The method employs extracting bone marrow by a simple intrusion into the donor's jawbone immediately before, during, or after a dental procedure.

A significant aspect and feature of the present invention is a method for extraction of bone marrow from the jawbone of young, healthy patients during dental procedures, including the removal of impacted or redundant third molars or bicuspids. This method allows for the ready accessibility of large quantities of bone marrow in multiple locations. An advantage to this procedure is that additional incisions, other than those already performed, are not necessary because access to the marrow is already present. Furthermore, because there is no need for additional incisions, virtually no additional pain or medical complications, other than that experienced by the routine dental procedure, is experienced by the patient.

According to this invention, the bone marrow can also be collection during other surgical procedures, such as dental implants. The anterior mandible is an extremely safe area to obtain bone marrow without risk to any other vital structures. Another area where large amounts of bone marrow are readily available, according to this invention, is the anterior boarder of the ramus of the mandible. The method also avoids the risk of visible scarring.

According to another embodiment of the present invention, the uses of bone marrow other than for storage includes use in bone regeneration procedures such as periodontal bone grafts, sinus lifts, and implant placement. Through the use of known multiplication procedures, this bone marrow can then be multiplied.

Another aspect of this invention allows for the genetic typing of the bone marrow collected to be put to other uses, such as cross-typing for organ transplants in traumatic circumstances.

An additional aspect of the invention is to treat the bone marrow before storage or transplantation in an effort to protect a patient from a relapse caused by undetected cancer cells.

Further treatment, when needed, of collected bone marrow encompassed by this invention includes the removal of blood and bone fragments. For instance, T-cell depletion can be used in allogeneic bone marrow to remove T-lymphocytes. Collected bone marrow can also be combined with a preservative, such as dimethyl sulfoxide ("DMSO") before storage and stored in a liquid nitrogen freezer until the day of transplantation. This technique, known as cryopreservation, allows the bone marrow to be preserved for a long period of time.

Cryopreservation permits bone marrow extracted during adolescence to be preserved throughout the lifetime of the donor. Currently, bone marrow transplantation is not used routinely in elderly adults because of the high risk of infection caused by the use of immunosuppressant drugs in use today. Thus, the availability of autologous bone marrow high in stem cells opens the door for a wide variety of treatment options, including anemia and osteoporosis.

The present invention also provides an apparatus for carrying out the method of this invention. One embodiment of the apparatus of the present invention includes a bone marrow extraction apparatus that has various sources of solution supply and collectors for the purpose of preparing the collected bone marrow for storage, preservation, and subsequent use.

In another embodiment, a dental apparatus for extracting bone marrow from a patient comprises a housing, means attached to the housing for extracting bone marrow from an extraction site, and means for collecting bone marrow extracted from the extraction site.

The extracting means may comprise a solid bone marrow extraction portion, the solid bone marrow extraction portion including a first and a second end, the first end being for collecting bone marrow. The extracting means may also comprise a liquid bone marrow extraction portion comprising a first end and a second end, the first end being for breaking bone marrow stroma and aspirating the liquid marrow.

In another embodiment, the extracting means comprises a bur and the collecting means comprises a passage in the housing. The collecting means may include a vacuum in communication with the passage in the housing.

The dental apparatus for extracting bone marrow from a patient may also comprise means for breaking up extracted bone marrow.

In another embodiment, the dental apparatus for extracting bone marrow from a patient comprises a housing having a cavity, a hollow shaft disposed in the cavity and having first and second ends, a bur attached to the first end of the hollow shaft, a beveled gear attached to the second end of the hollow shaft, and a drive gear matingly engaged to the beveled gear. A first passage is defined in the housing and is in communication with the hollow shaft for passing irrigation fluid to the extraction site. A second passage is defined in the housing and is in communication with the cavity for passing bone marrow from the cavity to a collection device. A vacuum may be placed in communication with the second passage.

In a further embodiment, the housing of the dental apparatus has a detachable portion, and at least a part of the second passage is defined in the detachable portion of the housing.

In another embodiment, the hollow shaft has a circumferential outer surface, and a spiral cutting blade for breaking up bone marrow is attached to the outer surface of the hollow shaft.

The collection device may comprise a tube in communication with the second passage and a container connected to the tube. The tube may include a valve for controlling a flow of bone marrow into the container.

A source for irrigation fluid may be placed in fluid communication with the first passage. The walls defining the cavity may have ridges for breaking up bone marrow prior to passage of the bone marrow through the second passage.

Further features and advantages will become apparent from the following and more particular description of the preferred and other embodiments of the invention, as illustrated in the accompanying FIGS. 1 through 4 in which like reference characters generally refer to the same parts or elements throughout the views, and in which:

BRIEF DESCRIPTION OF THE DRAWINGS

FIG. 1 is a side elevational view of one embodiment of the dental apparatus according to the present invention;

FIG. 2 is an enlarged, fragmentary sectional view of the embodiment of FIG. 1;

FIG. 3 is an enlarged, fragmentary sectional view of an alternative embodiment of the apparatus of the invention.

DETAILED DESCRIPTION OF THE INVENTION

Figure 4:
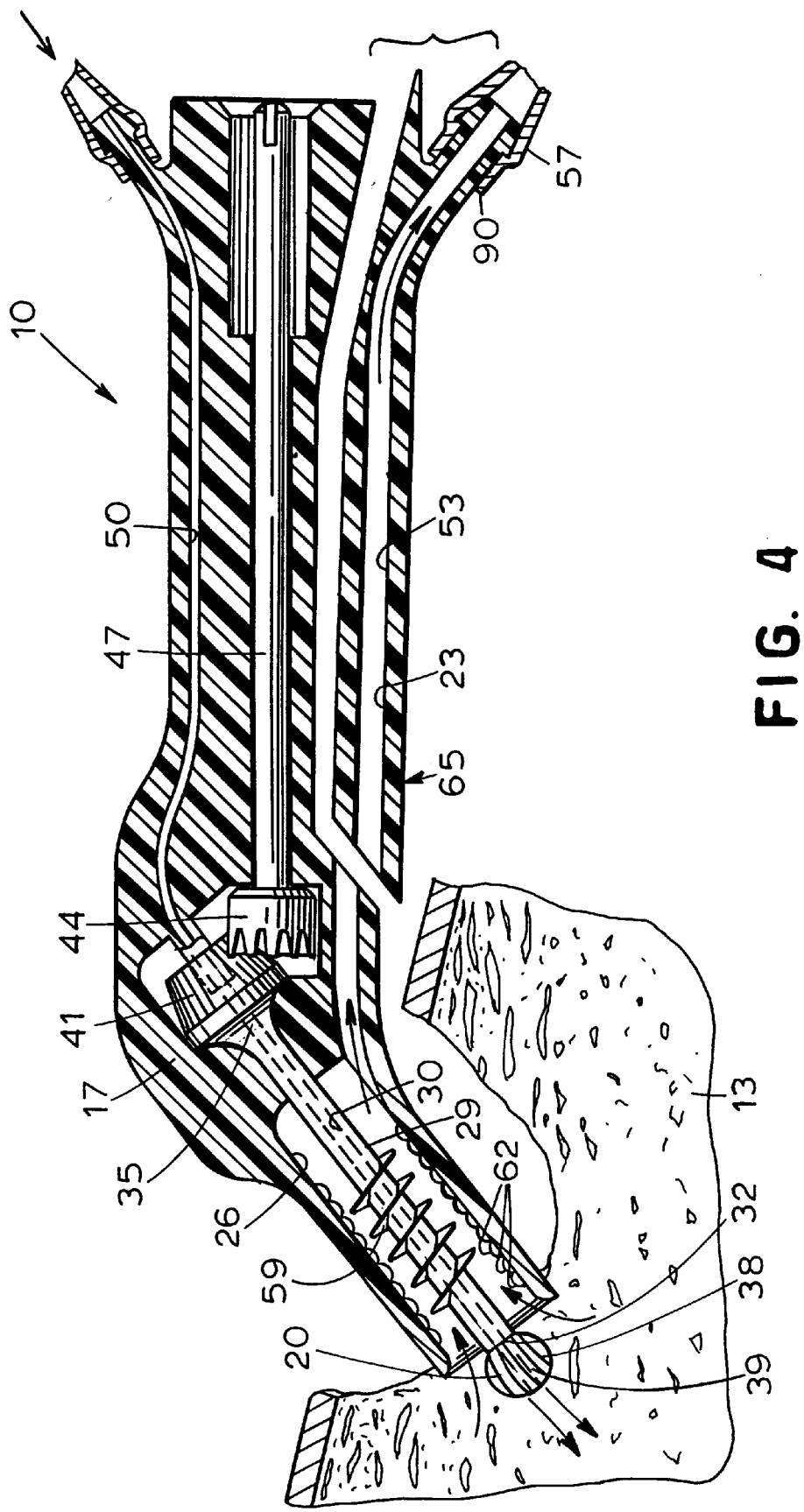
FIG. 4 is an enlarged, fragmentary sectional view of an alternative embodiment of the apparatus of the invention.

FIG. 1 illustrates the principles and concepts of a bone marrow extraction apparatus well adapted for use according to the invention. Shown in FIGS. 1 and 2 is an apparatus 10 capable of boring a hole in a jawbone 13 and extracting bone marrow therefrom. The apparatus 10 comprises a housing 17, structure 20 attached to the housing 17 for extracting bone marrow from an extraction site, and structure 23 for collecting bone marrow extracted from the extraction site.

The housing 17 has a cavity 26. A hollow shaft 29 having a conduit 30 and first and second end portions 32 and 35 is rotatably mounted in the housing 17 with the end portion 35 being disposed in the cavity 26. The end portion 32 includes a bur 38 having a cutting flute 39 for boring a hole in the jawbone 13. A beveled gear 41 is attached to the second end portion 35 of the hollow shaft 29. A drive gear 44 is matingly engaged to the beveled gear 41. The drive gear 44 is connected by a shaft 47 to an electrical motor, a pneumatic motor, or other suitable equipment (not shown) for driving the drive gear 44. The shaft 47 may be connected to the motor or other drive source by any feasible mechanical or other connection means. By engaging the shaft 47, the drive source rotates the shaft 47 so as to cause rotation of bur 38. As shown in FIG. 3, the shaft 47 may be adapted to be driven by a standard "E" motor.

The housing 17 has a first passage 50 in communication with the hollow shaft 29. The first passage 50 is for passing irrigation fluid to the extraction site. The irrigation fluid passes through the passage 50 and then through the conduit 30 to the extraction site. The irrigation fluid cools the extraction site and adds liquid to the extracted fluids and solids to facilitate removal by suction. A source 51 (FIG. 1) of irrigation fluid may be connected to the housing 17 so that the source 51 is in communication with the first passage 50.

The housing 17 has a second passage 53 in communication with the cavity 26. The second passage 53 is for passing bone marrow from the cavity 26 to a collection device 56 (FIG. 1).

A suction tube 57 may be connected to the second passage 53 for extracting solid bone marrow from the medullary cavity of the donor. The rotating bur 38 and the suction tube 57 are preferably detachably connectible to the housing. The housing 17 may be a hand-held power unit. However, while the housing 17 may be formed in a generally cylindrical handle-type configuration as shown in FIG. 1, such apparatus may be of other forms, including a pistol grip-type configuration (not shown).

Apparatus 10 may include structure for breaking up bone marrow into smaller particles prior to the entry of the particles into the second passage 53. For example, a spiral cutting blade 59 may be attached to the outer surface of the hollow shaft 29 for breaking up particles while the hollow shaft 29 rotates. Additionally or alternatively, the cavity 26 may be defined by walls having ridges 62. The ridges 62 break up the bone marrow into smaller particles as the particles pass through the cavity 26 into the second passage 53.

As shown in FIG. 4, the housing 17 may have a detachable portion 65. At least a part of the second passage 53 is defined in the detachable portion 65. Alternatively, the second passage 53 may be connected to the outside portion of the housing 17 of FIGS. 2 and 4.

The suction tube 57, which includes an integral valve 68 (FIG. 1), is attached to a vacuum source 71 (shown schematically in FIG. 1) at one end and a suction tip (not shown) at the other end. The integral valve 68, which comprises a housing and a pivotal obturator, permits an operator of the apparatus to selectively produce suction through the suction tube 57 with one hand. See U.S. Pat. No. 5,295,830.

A vacuum source 74 (FIG. 1) withdraws solid and liquid bone marrow from the medullary cavity into the suction tube 57, which transfers the solid and liquid bone marrow to the collection device 56.

The apparatus 10 of FIGS. 1 and 2 could be used immediately before, during, or after a dental procedure or dental surgery. Thus, an adaption of the apparatus 10 described above which does not contain the rotating bur 38 is also in accordance with the present invention. Preferably, the rotating bur 38 incorporates an internal vacuum. More preferably, the configuration would be an entirely disposable unit designed to fit on a standard dental straight hand piece or to fit on a standard "E", motor, either air driven or electric.

A biopsy needle 85, shown schematically in FIG. 1, may be used in conjunction with the apparatus 10. One configuration for utilizing the biopsy needle 85 includes a tube 80 (FIG. 1) in communication with the valve 68 and the suction tube 57. The biopsy needle 85 may be connected at an end of the tube 80.

The valve 68 may be used to control whether suction is produced through the tube 57 (and therefore the apparatus 10), the tube 80, or, if desired, both the tube 80 and the tube 57 simultaneously. When suction is produced in the tubes 57, 80 simultaneously, the biopsy needle 85 may be positioned adjacent the extraction site to provide extra suction and to otherwise assist the apparatus 10 in extracting bone marrow.

Alternatively, an end 90 of the tube 57 may be removed from the housing 17. A biopsy needle may be attached to the end 90 of the tube 57. The biopsy needle may then be positioned adjacent the extraction site to assist in bone marrow extraction. In this configuration, all suction would be provided by the biopsy needle, because the apparatus 10 would not be in communication with the vacuum source 74.

A preferred embodiment has a rotating bur 38 that is oversized for vacuum collection. The rotating bur 38 may be made of, for example, carbides, stainless steel, or plastic, and comprises at least one large opening similar to internal irrigating burs used for implants, with a cuff as either an integral part of a disposal hand piece or attachable to the bur 38, allowing free rotation of the forward portion only. The rotating bur 38 is connected to a vacuum hand piece similar to the housing 17, such as disclosed in U.S. Pat. No. 3,863,635. The rotating bur 38 may also be contained within the suction tube 57.

The liquid bone marrow can be obtained from dental extraction sites using a heavy metal blunt instrument following dental extraction to compress the bone alone and integrated vacuum to collect the bone marrow.

The apparatus 10 may include a solid bone marrow extraction portion having a first end and a second end. The first end is for collecting bone marrow. The apparatus 10 may also include a liquid bone marrow extraction portion comprising a first end and a second end. The first end is for breaking bone marrow stroma and aspirating the liquid marrow. Some conventional biopsy needles may be used to provide the solid bone marrow extraction portion and the liquid bone marrow extraction portion.

The apparatus of FIG. 2 may further comprise an elongated stainless steel solid marrow pushing probe to express a solid marrow specimen outside the cavity 26 after the procedure. (Not shown in FIG. 5.) One example is shown in U.S. Pat. No. 5,012,818.

The extraction of bone marrow from the jawbone during a dental procedure provides an advantage to the dental procedure alone in that it decreases the percentage of extraction sites experiencing dry sockets. This is due to the perforation of the compressed bone of the tooth socket.

A preferred embodiment of the present invention provides for a bone marrow extraction apparatus which effects the removal of bone marrow and bone marrow fluid from a donor at the jawbone and mixes the removed bone marrow with a suitable form of solution, such as a mixture of anticoagulant and saline or electrolytic solution. The bone marrow and bone marrow fluid removed from the donor are then transferred either into a cell separator or a suitable collection bag, such as the collection chamber 56, so as to permit separation of the bone marrow and fluid for subsequent processing and long-term storage. The collected bone marrow may also be used for the subsequent reinjection into the donor in future bone marrow transplantation procedures.

In the removal of the bone marrow from the donor, a solution consisting of heparin or other anticoagulant compositions, together with a saline solution, can be mixed with the bone marrow and bone marrow fluid before, during, and/or after being transferred into separating or collecting means.

The collection device 56 may be a bag containing chemicals for preserving bone marrow. The chemicals may be in the bag prior to the withdrawal of bone marrow from the jaw of a patient. In this manner, after bone marrow has been collected, the device 56 can be stored cold directly. Additionally or alternatively, chemicals can be added to the collection device 56 during or after collection of bone marrow to preserve the bone marrow. Suitable means for adding chemicals to a container such as the collection device 56 are well known in the art and may include penetrable membranes at specific locations on the collection device 56.

The collection device 56 is preferably collapsible so that air may be removed after collection has occurred. Removal of air increases the useful life of the bone marrow.

From the foregoing, disclosed is a bone marrow collection apparatus which is easily adapted to conventional dental or medical equipment. A technical advantage of the extraction-removing equipment of the invention is that bone marrow can be more quickly removed than conventional extraction procedures.

The dental apparatus according to the invention is not limited to that specifically disclosed and may comprise tools other than that described herein. Andre Schroeder et al., *Oral Implantology,* pages 66–71, 118–151, 178–187, 202–217, and 228–243 (George Thieme Verlag, 1988), discloses additional tools that are capable of boring holes in jawbones. Further, U.S. Pat. No. 4,564,374 discloses a device that is capable of extracting both solid and liquid bone marrow. Adaptation of this device may also be used in accordance with the present invention.

In a preferred method according to this invention, a donor is positioned in a dental examination chair. A hole is formed in the donor's jawbone before, during, or immediately after a conventional dental procedure using the boring portion or bur 38 of the apparatus according to the present invention. The boring portion or bur 38 can also be used to break up the bone marrow after a hole is formed. The area of marrow extraction is sterilized with an antiseptic solution. The entire procedure of obtaining both solid and liquid bone marrow can be accomplished in less than one to two minutes. The large lumen is introduced into the previously made bore hole and pushed into the medullary cavity. The large lumen is pushed further into the marrow cavity with forward pressure in order to obtain solid marrow. The large round bur can simultaneously irrigate and vacuum.

Liquid bone marrow sample is obtained by applying a negative pressure in the small lumen of the suction tube 57 using a vacuum source (not shown). This results in the breaking of marrow stroma and the release of fluid marrow.

Collagen resorbable membranes or plugs can be used to cover the access to the bone marrow. This assures replacement of bone with bony and not fibrous tissue.

In summary, this invention overcomes many inconveniences of the existing bone marrow extraction methods. First, this is a new method of obtaining both solid and liquid marrow in a single procedure. Secondly, the apparatus allows reducing the procedure of extracting and collecting into one step.

While the invention has been described in detail in the drawings and foregoing description, the same is to be considered as illustrated and not restrictive in character. It being understood only in the preferred embodiment and methods have been shown and described, and all changes and modifications that come within the spirit of the invention are desired to be protected.

What is claimed is:

1. A dental apparatus for extracting bone marrow from a patient, the apparatus comprising:
    a housing having a cavity, a first passage for passing irrigation fluid to an extraction site, and a second passage for passing bone marrow from the cavity to a collection device, the second passage being in communication with the cavity;
    a hollow shaft disposed in the cavity and having first and second ends, the hollow shaft being in communication with the first passage;
    a bur attached to the first end of the hollow shaft;
    a beveled gear attached to the second end of the hollow shaft; and
    a drive gear matingly engaged to the beveled gear.

2. The dental apparatus of claim 1, wherein:
    the housing has a detachable portion;
    at least a part of the second passage is defined in the detachable portion of the housing.

3. The dental apparatus for extracting bone marrow according to claim 1 further comprising a vacuum in communication with the second passage.

4. The dental apparatus for extracting bone marrow according to claim 1 wherein:
    the hollow shaft has a circumferential outer surface; and
    a spiral cutting blade for breaking up bone marrow is attached to the outer surface of the hollow shaft.

5. The dental apparatus for extracting bone marrow according to claim 1 wherein:
    the collection device comprises a tube in communication with the second passage and a container connected to the tube.

6. The dental apparatus for extracting bone marrow according to claim 5 wherein:
    the tube comprises a valve for controlling a flow of bone marrow into the container.

7. The dental apparatus for extracting bone marrow according to claim 1 wherein:
    a source of irrigation fluid is in fluid communication with the first passage.

8. The dental apparatus for extracting bone marrow according to claim 1 wherein:
    the cavity is defined by walls having ridges for breaking up bone marrow prior to passage of the bone marrow through the second passage.

* * * * *